(12) United States Patent
Prince

(10) Patent No.: US 11,696,722 B2
(45) Date of Patent: **\*Jul. 11, 2023**

(54) MULTIPLE TEST APPLICATOR

(71) Applicant: Ty L. Prince, Knoxville, TN (US)

(72) Inventor: Ty L. Prince, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/992,125

(22) Filed: Nov. 22, 2022

(65) Prior Publication Data

US 2023/0080432 A1 Mar. 16, 2023

Related U.S. Application Data

(63) Continuation-in-part of application No. 17/468,132, filed on Sep. 7, 2021, now Pat. No. 11,369,782, and a continuation-in-part of application No. 17/402,413, filed on Aug. 13, 2021, now Pat. No. 11,517,249.

(51) Int. Cl.
*A61B 5/00* (2006.01)

(52) U.S. Cl.
CPC ........... *A61B 5/411* (2013.01); *A61B 2560/06* (2013.01)

(58) Field of Classification Search
CPC ............................ A61B 5/411; A61B 2560/06

USPC ......................................................... 600/556
See application file for complete search history.

(56) References Cited

U.S. PATENT DOCUMENTS 5,551,441 A * 9/1996 Pitesky ................ A61B 17/205
600/556

* cited by examiner

*Primary Examiner* — Alex M Valvis
*Assistant Examiner* — Chanel J Jhin
(74) *Attorney, Agent, or Firm* — Gerald R. Black, Esq.

(57) ABSTRACT

A multiple test applicator has a first and second scratching barb in cooperative engagement with each other and a first and second reservoir in a fluid tray each filled with a first and second allergen. During allergen loading, the first allergen is loaded onto the first scratching barb as the second allergen is loaded onto the second scratching barb. Then, during allergen deposition the applicator is removed from the fluid tray and the first scratching barb moves laterally across the patient's skin as the second scratching barb moves laterally across the patient's skin toward the first scratching barb. The first scratching barb then scratches the epidermis at a first test site as a trace amount of the first allergen is deposited into a first site as the second scratching barb scratches a second site as a trace amount of the second allergen seeps into the second site.

26 Claims, 14 Drawing Sheets

DETAIL "A"
ALLERGEN LOADING

ALLERGEN DEPOSITION

RELAXED STATE

COMPRESSED STATE

COMPRESSED STATE

BARB TILTED UP

BARB TILTED UP

BARB TILTED UP

DETAIL "B"
ALLERGEN LOADING

RELAXED STATE

COMPRESSED STATE

RELAXED STATE

BARB TILTED DOWN

BARB TILTED DOWN

BARB TILTED DOWN

MULTIPLE TEST APPLICATOR

CROSS-REFERENCE TO RELATED APPLICATIONS

This Application is a continuation-in-part to and claims priority to U.S. patent application Ser. No. 17/402,413 entitled "Multiple Allergen Test Applicator" filed on Aug. 13, 2021; U.S. patent application Ser. No. 17/468,132 (now U.S. patent Ser. No. 11/369,782) entitled "Methods for Administering Multiple Allergens" filed on Sep. 7, 2021; and U.S. Provisional Application No. 63/106,793, entitled "Single and Multiple Allergen Skin Testing System" (Prince) filed on Oct. 28, 2020.

FIELD OF USE

The present invention relates to new multiple test applicators for use with allergens in the skin of a patient, and more particularly, to new applicators for conducting multiple allergy scratch tests.

BACKGROUND OF THE INVENTION

There is an increasing population of allergy disease sufferers. Accordingly, there is a growing need to identify these people and their allergy issues, and to treat these disorders.

The medical technician administering these skin tests may often need to apply a relatively large number of different allergens to the skin of a patient simultaneously. To perform skin tests of this type, the medical technician removes the skin-test device with a small amount of allergen deposited on the sharp pointed testing tips and applies the allergen to the patient in a predetermined sequence.

Some skin testing applicators and systems known to treat patients include:

U.S. Pat. No. 6,554,777 (Hein, Jr.) discloses a multi-site skin-test system. The system includes a reservoir tray and strips of interconnected reservoir caps inserted into upper portions of the reservoirs. The caps each include a generally conically shaped hole. Connection members connect the caps of a strip to one another. The strips of caps are pressed into tightly fitting upper portions of reservoirs having upwardly facing ledge surfaces for supporting downwardly facing bottom surfaces of the caps. The outer side surfaces of the caps and the inner surfaces of the upper portions of the reservoirs are substantially the same size to provide a tight fit.

U.S. Pat. No. 9,597,030 (Smollar) depicts an allergy testing kit containing a plurality of allergy testing applicators, an allergy testing tray, and a plurality of allergen bottles each containing an allergen. Each of the applicators contains an elongated handle, a plurality of arms extending from the elongated handle and disposed in an asymmetrical configuration, and a plurality of legs with tines extending from each of the arms. The allergy testing tray contains a main body having an underside and a top surface, a cover for locking with the main body and a plurality of reservoirs extending from the underside of the main body. The reservoirs each have a chamber with an opening extending from the top surface. The reservoirs are disposed in different groups and each group has an asymmetrical configuration matching that of the applicator.

U.S. patent application Ser. No. 11/885,086 (Schindlbeck; et al.) depicts a device for performing an allergy test. The device comprises a container assembly including several containers designed to receive the allergens, and a mark transferable onto the skin which is used to associate specific allergens to specific allergy sites on the skin of a living being undergoing an allergy test. The device aims at improving so that the allergy test sites on the skin can be constantly marked very legibly, and so that the corresponding marks can be readily eliminated from the skin immediately after the allergy test.

U.S. patent application Ser. No. 10/558,943 (Ronborg; et al.) discloses an allergy tester for delivering a diagnostic agent to the skin or mucosa of a patient. A chamber filled with the diagnostic agent is separate from the housing with a rod capable of transferring the diagnostic agent to the animal. The chamber is connected to the housing with the rod before transfer of diagnostic agent.

Since many different allergens need to be screened for a particular patient, it becomes necessary to minimize patient discomfort while accumulating patient data so that the proper course of treatment can be identified.

What is needed is a multiple test applicator that will replace needle pricks that are commonly used: a simple, economical, and reliable scratch testing applicator in which multiple allergens can be tested simultaneously on the skin of a patient which minimizes any cross contamination of the allergens, that simplifies the handling of the applicator and provides results that are easily observable.

The objectives of this multiple test applicator are to provide systems that significantly reduce the possibility of errors in reading the test results while reducing false positives, and minimizing patient discomfort, that is cost-effective, and is easy to use and manufacture.

Certain other objects will become apparent to those skilled in the art from the following description of preferred embodiments of the invention taken in connection with the accompanying drawings.

SUMMARY OF THE INVENTION

The multiple test applicator of the present invention addresses these needs and objectives.

The system of the present invention uses a multiple test applicator that is in cooperative engagement with a fluid tray to administer a plurality of allergens simultaneously into the skin of a patient.

The multiple test applicator has a plurality of scratching barbs positioned on the multiple test applicator each being aligned with one of a plurality of reservoirs. Each reservoir in the fluid tray preferably contains an allergen or some other testing fluid.

The applicator of the current invention involves allergen loading (when the scratching barbs are loaded with allergen fluid) followed by allergen deposition (where trace amounts of each allergen are deposited into a scratch on the epidermis layer of the skin of the patient created by the scratching barb).

A multiple test applicator has a first and second scratching barb in cooperative engagement with each other and with a first and second reservoir in a fluid tray each filled with a first and second allergen. During allergen loading, the first allergen is loaded onto the first scratching barb as the second allergen is loaded onto the second scratching barb.

Then, during allergen deposition the multiple test applicator is removed from the fluid tray and the first scratching barb moves laterally across a first section of the skin of the patient as the second scratching barb moves laterally across a second section of the skin of the patient toward the first scratching barb. The first scratching barb then scratches the epidermis at a first test site as a small amount of the first allergen is deposited into a first site as the second scratching barb scratches a second site as a small amount of the second allergen seeps into the second site. The first scratch is preferably formed in the first section of the skin and the second scratch is preferably formed in the second section of the skin.

In an alternative embodiment, the multiple test applicator has the scratching barbs pointed downward toward the bottom of the fluid tray during allergen loading. A first side handle is cooperatively engaged with a second side handle. After allergen loading is completed, inward pressure is applied by an operator holding in one hand the multiple test applicator. The first side handle and the second side handle are squeezed together after the allergen loading is completed and prior to the allergen deposition. As the first and second scratching barbs are positioned upon the skin of the patient in the compressed state, with the expanded state of the first and second scratching barbs shown in phantom. As the first scratching barb moves substantially in a lateral direction across a first section of the skin as the second scratching barb moves substantially in a lateral direction across a second section of the skin away from the first scratching barb. The first scratch is preferably generated in the first section of the skin as the second scratch is preferably generated in the second section of the skin.

During allergen loading, a different allergen is loaded onto each respective scratching barb from each respective reservoir. Each scratching barb is designed to retain a trace amount of fluid.

The multiple test applicator fits into one hand of a medical technician administering the test enabling one-handed operation.

The medical test applicator is then removed from the fluid tray and repositioned onto the skin of the patient for allergen deposition.

During allergen deposition, each scratching barb scratches the epidermis layer of the skin of the patient at each respective test site as a trace amount of each respective allergen seeps into each respective test site from each scratching barb.

The multiple test applicator is preferably made of a compressible material, the multiple test applicator having a relaxed state and a compressed state. The multiple test applicator is in the relaxed state while in allergen loading position when the multiple test applicator is cooperatively engaged with the fluid tray. The multiple test applicator preferably includes a first finger grip disposed on a first side frame and a second finger grip disposed on an opposing side frame.

Pressure applied by a thumb positioned on the first finger grip disposed on the first side frame and an index finger of the same hand disposed on a second finger grip disposed on the opposing side frame enable repositioning of the multiple test applicator from the relaxed state to the compressed state.

Applying pressure in an inward direction to the first side handle toward the second side handle facilitates movement of the first scratching barb toward the second scratching barb. Relaxing pressure applied in an inward direction of the first side handle toward the second side handle facilitates movement of the first scratching away the said second scratching barb.

In a first preferred embodiment, the scratching barbs project in an upward direction away from the fluid tray. The allergen deposition occurs when the multiple test applicator is repositioned onto the skin of the patient and the multiple test applicator is in the compressed state.

In a second preferred embodiment, the scratching barbs project in a downward direction toward the fluid tray. The multiple test applicator is repositioned from a compressed state to a relaxed state when placed onto the skin of the patient in the allergen deposition position.

For allergies to initially develop, the body must be exposed to an allergen, that prompts the body to initiate an immune response.

In intradermal skin testing, a medical professional injects a tiny amount of allergen into the outer layer or epidermis of the patient. The immediate positive skin reaction reaches a peak in about fifteen minutes, and is a pale central area surrounded by redness (a flare) and a bump or swelling (a wheal).

In addition to the allergens in question, skin testing is also performed with a positive control (histamine) that should always cause a skin reaction, and a negative control (saline), that should not cause a reaction. A test is positive if the allergen causes a wheal 3 mm greater than the negative control, and if the skin has a response to the histamine, as well.

The allergic reaction is measured immediately after the application of the allergen. The information is a direct measure of the allergy reaction occurring under the skin. The information on each site is presented to the physician to compare against visual observations. A determination of the patient susceptibility to each allergen is determined by the physician and a course of future action is planned. A positive skin test does not predict the severity of an allergic reaction. A negative skin test usually means the patient is not allergic.

In general, allergy skin tests are reliable for diagnosing allergies to airborne substances, such as pollen, pet dander and dust mites. Skin testing may help diagnose food allergies, but because food allergies can be complex, additional procedures may be required.

The multiple allergen testing system of the present invention is designed to minimize any cross contamination of the various allergens.

For a complete understanding of the multiple test applicator of the present invention, reference is made to the accompanying drawings and description in which the presently preferred embodiments of the invention are shown by way of example. As the invention may be embodied in many forms without departing from spirit of essential characteristics thereof, it is expressly understood that the drawings are for purposes of illustration and description only and are not intended as a definition of the limits of the invention.

BRIEF DESCRIPTION OF THE DRAWINGS

FIG. 1013 depicts an end view of the single test applicator of FIG. 10A.

DETAILED DESCRIPTION OF THE PREFERRED EMBODIMENTS

Figure 1:
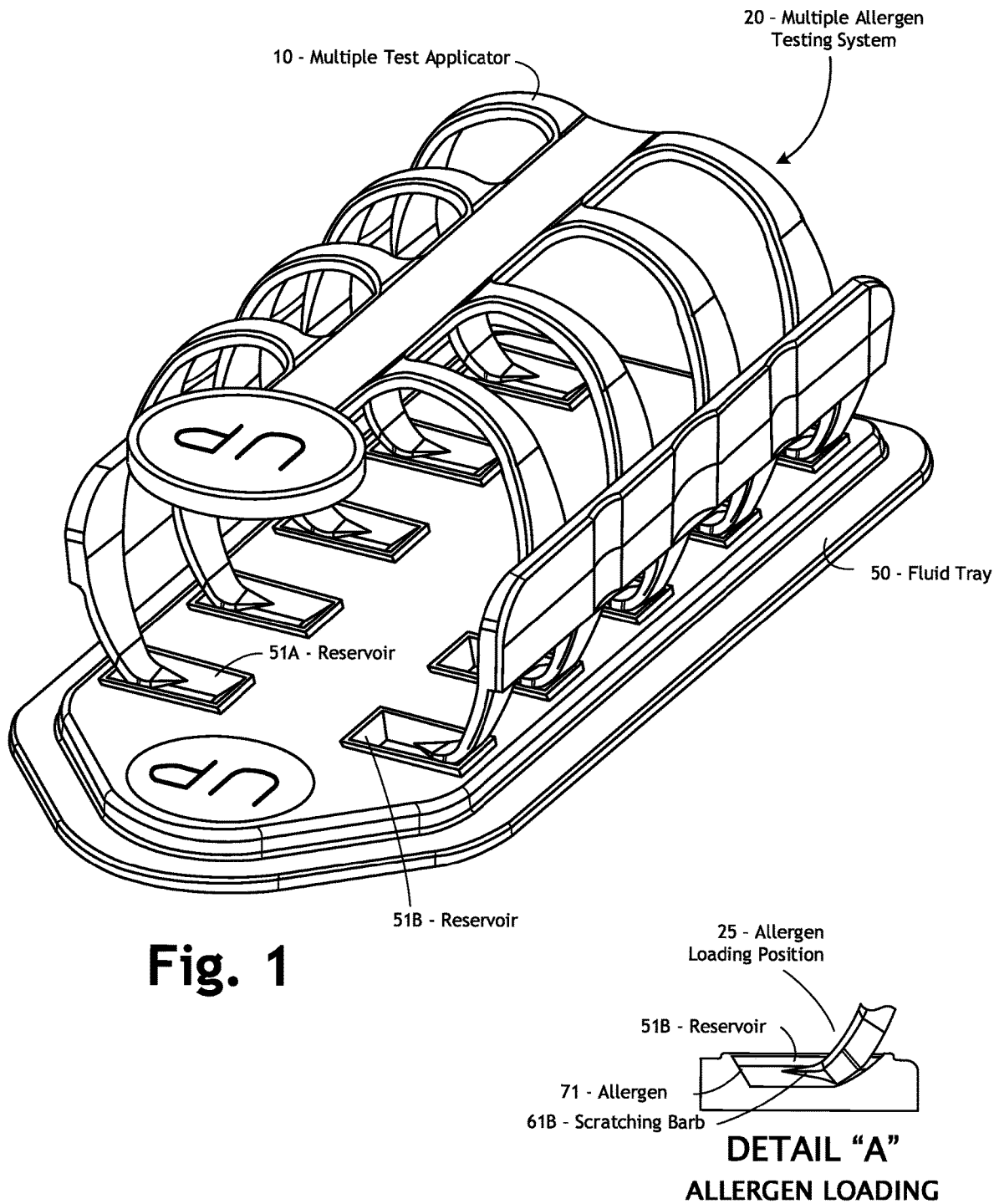
FIG. 1 depicts an assembly view of the multiple test applicator and system of the present invention comprising a first preferred embodiment of the multiple test applicator having ten applicators cooperatively engaged with a fluid tray, the multiple test applicator being disposed on the fluid tray; and DETAIL "A" depicts an exploded side view of the scratching barb projecting upward relative to the fluid tray disposed in a reservoir of the fluid tray during allergen loading, the reservoir being partially filled with an allergens.

Referring now to the drawings, FIG. 1 depicts an assembly view of a first preferred embodiment of multiple allergen testing system [20] comprising of a first preferred embodiment of the multiple test applicator [10] including a first scratching barb [61A] in cooperative engagement a first fluid reservoirs [51A] and a second scratching barb [61B] in cooperative engagement with a second fluid reservoir [51B] both fluid reservoirs [51A and 51B] positioned in a fluid tray [50].

DETAIL "A" depicts an exploded side view of the scratching barb [61B] positioned in a reservoir [51B] of the fluid tray [50] while in the allergen loading position. The reservoir [51B] is partially filled with allergen [71]. Here, the scratching barbs [61A and 61B] project in a downward direction pointing to the bottom of the fluid tray [50]. The multiple test applicator [10] is enabled to reposition from the compressed state to the relaxed state when placed on the skin of the patient [80] during allergen deposition [92].

Figure 3:
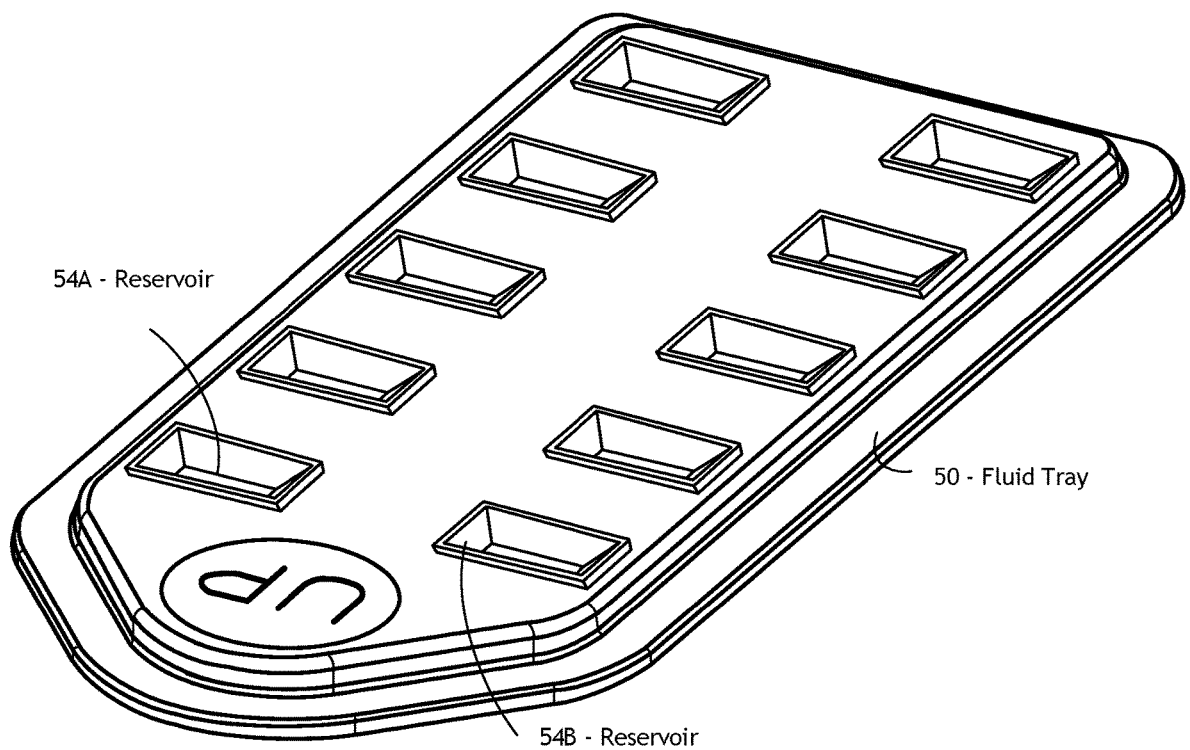
FIG. 3 depicts a detailed assembly view of the fluid tray for use with the multiple test applicator of FIG. 1 complete with ten reservoirs.

A first scratching barb [61A] is in cooperative engagement with a first reservoirs [51A] of a fluid tray [50], and a second scratching barb [61B] is in cooperative engagement a second reservoir [51B] of the fluid tray [50]. The fluid tray is shown in FIG. 3. Each reservoir preferably retains a different liquid for skin testing.

When allergens are placed into respective reservoirs [51A and 51B] in the fluid tray [50], care is taken to avoid using excess amounts of the allergens [71] which may cause cross contamination of allergens. The size of the reservoirs and the distance between adjacent reservoirs are designed to minimize any cross contamination of the allergens.

Figure 2:
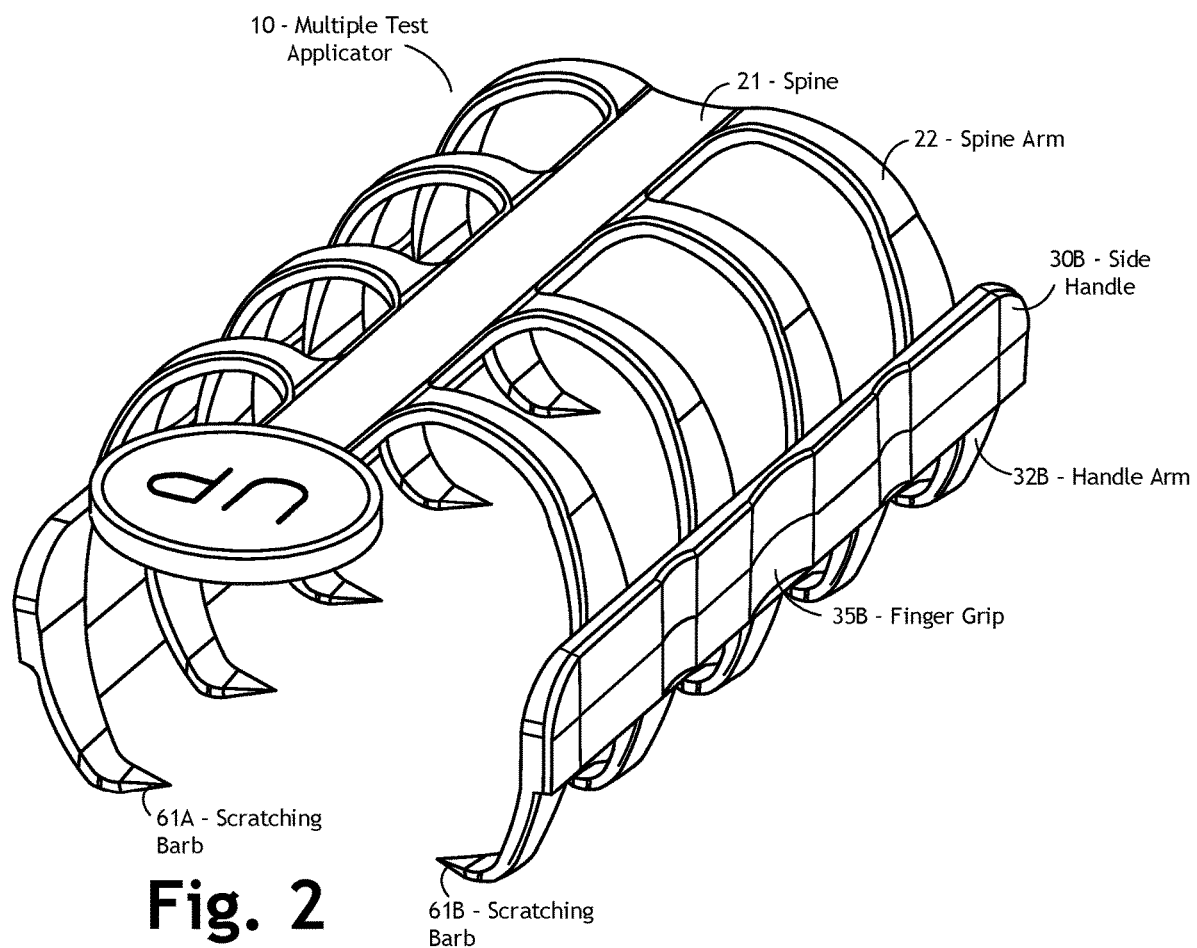
FIG. 2 depicts an exploded view of the multiple test applicator of FIG. 1.

FIG. 2 depicts the multiple test applicator [10] as shown in FIG. 1. A first scratching barb [61A] is in cooperative engagement with reservoir [51A] of the fluid tray [50] and a second scratching barb [61B] is in cooperative engagement with reservoir [51B] of the fluid tray [50].

The first scratching barb [61A] opposes the second scratching barb [61B], and the first scratching barb [61A] is in cooperative engagement with the second scratching barb [61B].

The first scratching barb [61A] projects in an upward direction relative to the bottom of the fluid tray [50] when disposed in the first reservoir [51A] and the second scratching barb [61B] projects in an upward direction relative to the bottom of the fluid tray [50] when disposed in the second reservoir [51B].

The application of pressure in an inward direction of the first side handle [30A] toward the second side handle [30B] facilitates movement of the first scratching barb [61A] toward the second scratching barb [61B]. The relaxation of pressure applied in an inward direction of the first side handle toward the second side handle facilitates movement of the first scratching [61A] away the said second scratching barb [61B].

Allergens are inserted into containment reservoirs in the fluid tray [50]. The fluid tray [50] may also be preloaded. The multiple allergen testing system [20] is removed from its sterile package. The method for administering a plurality of allergens into skin of a patient involves a two-stage positioning process: (1) an allergen loading, and (2) an allergen deposition.

After allergen loading is complete, the applicator [10] is removed from the fluid tray [50] and placed onto the skin of the patient [80].

The testing arms are pulled toward the center of the applicator from both sides, raising up the skin of the patient. The pair of skin lifting pads [45A and 45B] are sandwiched about each scratching barb [61B or 61B]. The pair of skin lifting pads [45A and 45B] lift the skin and limit the depth of penetration of each scratching barb [61A or 61B]. From this position, the scratching barb [61A or 61B] is pulled up and away from the skin of the patient [80]. This action creates a pair of small scratches [91A and 91B] on the skin of the patient [80] inserting a small amount of allergen [71] under the skin.

While in the allergen loading position, the multiple test applicator [10] is in the relaxed state.

Figure 4:
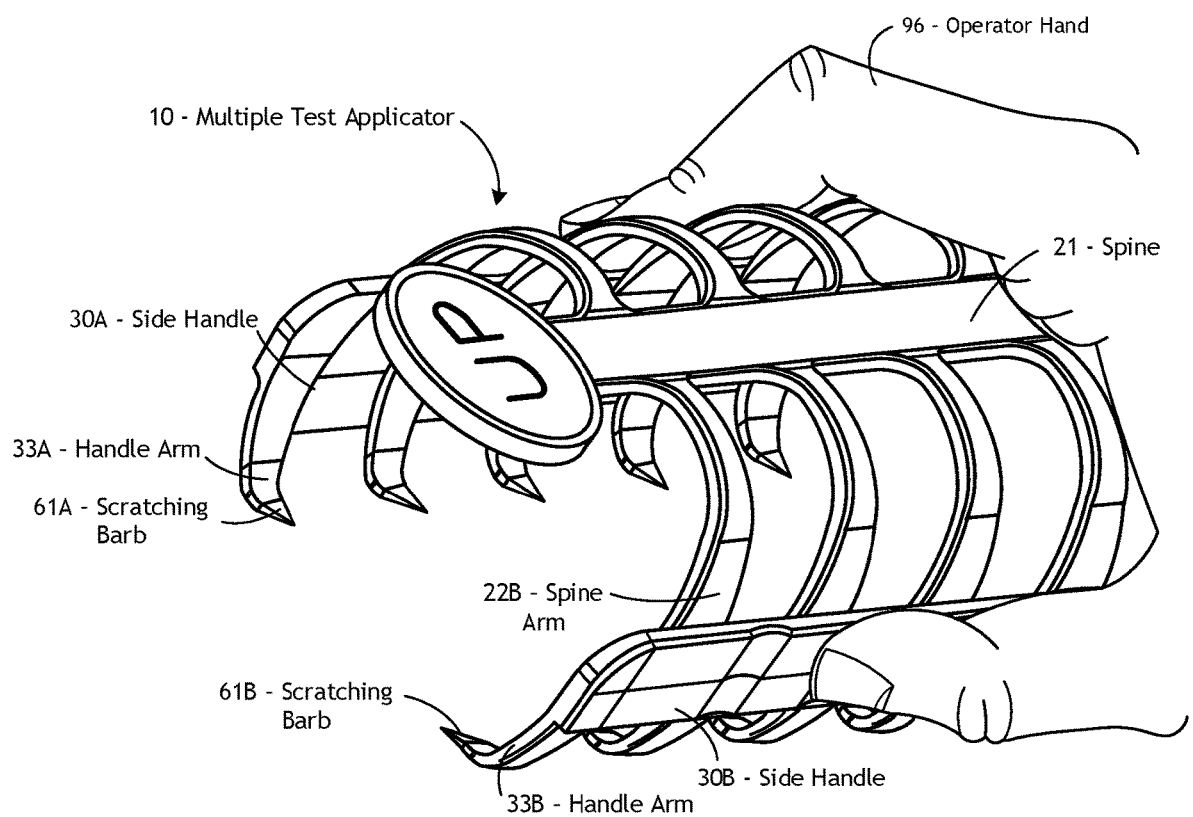
FIG. 4 depicts the multiple test applicator of FIG. 2 held in one hand by an operator, with the thumb positioned on a first finger grip on a first side frame and the index finger of the same hand positioned on an opposing finger grip on an opposing side frame, the first side frame opposing the second side frame.

FIG. 4 depicts the first preferred embodiment of the multiple test applicator [10] held in one hand by a medical technician, with the thumb positioned on a first finger grip [35A] on a first side handle [31A] and the index finger of the same hand positioned on a second finger grip [35B] on a second side handle [31B], the first side handle [31A] opposing the second side handle [31B].

The multiple test applicator [10] is in the relaxed state while in allergen loading position [25] when the multiple test applicator [10] is in cooperative engagement with the fluid tray [50]. The multiple test applicator [10] is preferably sized to be held in one hand of a medical technician administering the allergen skin testing. The pair of finger grips [35A and 35B] are positioned on opposing sides of each opposing side handle [30 and 31]. The medical technician grasps the applicator [10] by the pair of opposing finger grips [35A and 35B] in her hand during the allergen loading process and the allergen depositing process by placing her thumb on one finger grip [35A] and her forefinger of the same hand on the other finger grip [35B]. The applicator involves one hand of an operator [96] positioning a multiple test applicator [10] onto a loading tray [50] during the allergen loading.

The use of the finger grips [35A and 35B] to move the multiple test applicator [10] from the relaxed state to the compressed state and then back again to the relaxed state enables one-handed operation by the operator.

Multiple allergens are retainable in the reservoirs [51A and 51B] of the fluid tray [50]. Allergens are initially selected and placed into the individual containment reservoirs [51A and 51B] of the fluid tray [50], and care is taken not to use an excess amount of the allergens. The multiple test applicator [10] has multiple scratching barbs [61A and 61B]. During the allergen loading each scratching barb [61A or 61B] is positioned in a reservoir [51A or 51B] containing an allergen [71].

Figure 5:
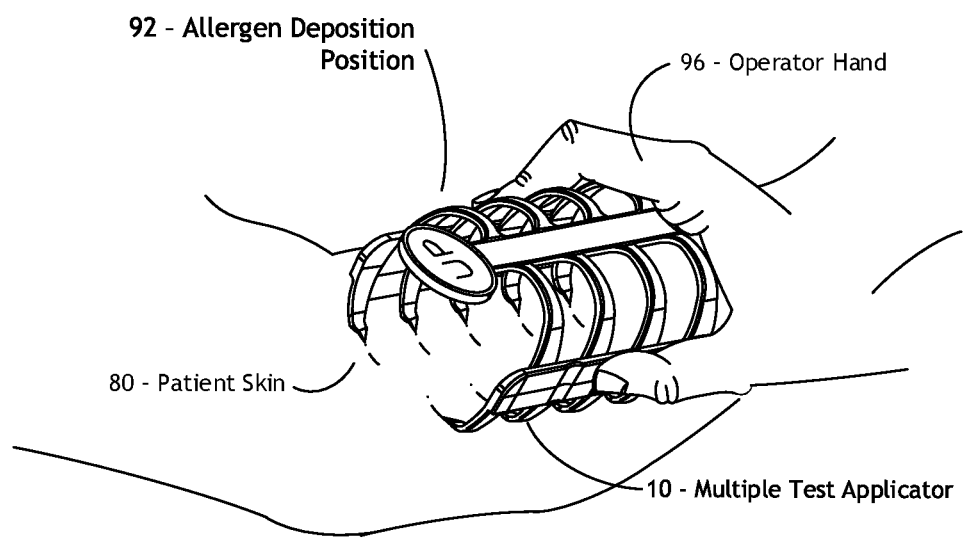
FIG. 5 depicts the multiple test applicator of FIG. 2 held in one hand of the operator as the allergens are deposited under the skin on a forearm of a patient.

FIG. 5 depicts the multiple test applicator [10] held in one hand of the medical technician as the allergens are deposited under the skin on a forearm of a patient [80].

The operator [96] using one hand then repositions the multiple test applicator [10] onto the skin of the patient [80] for allergen deposition [92].

During allergen deposition [92], the medical technician uses the same hand as in the allergen loading enabling one-handed operation throughout the entire process. The first scratching barb [61A] facilitates a first scratch on a first epidermis layer of the patient while in the during allergen deposition [92] relative to the skin of the patient [80]. The second scratching barb [61B] facilitates a second scratch on a second epidermis layer of the patient while during allergen deposition [92] relative to the skin of the patient [80].

After being repositioned from the barb allergen loading position [25] once the first and scratching barbs are loaded with some of the allergens. The multiple test applicator [10] is primed to deposit the allergens in the scratches on the skin of the patient [80].

Figure 6A:
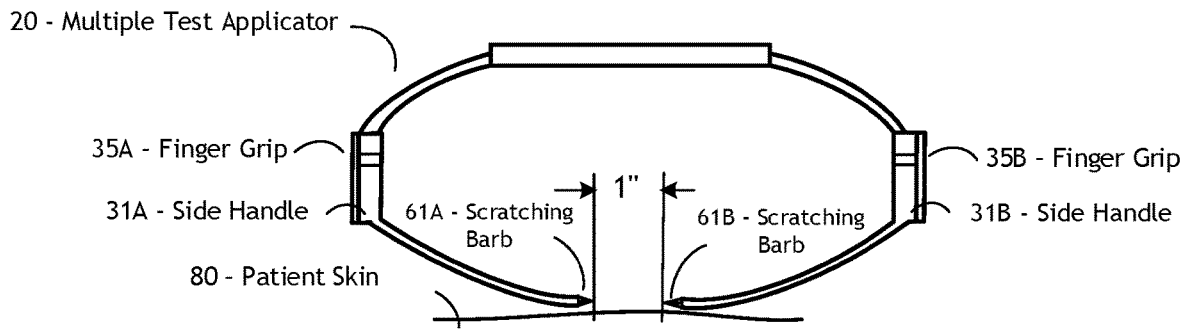
FIG. 6A is a front view of the multiple test applicator of FIG. 2, the multiple test applicator being in an expanded position, the scratching barbs resting upon the skin of the patient.
Figure 6B:
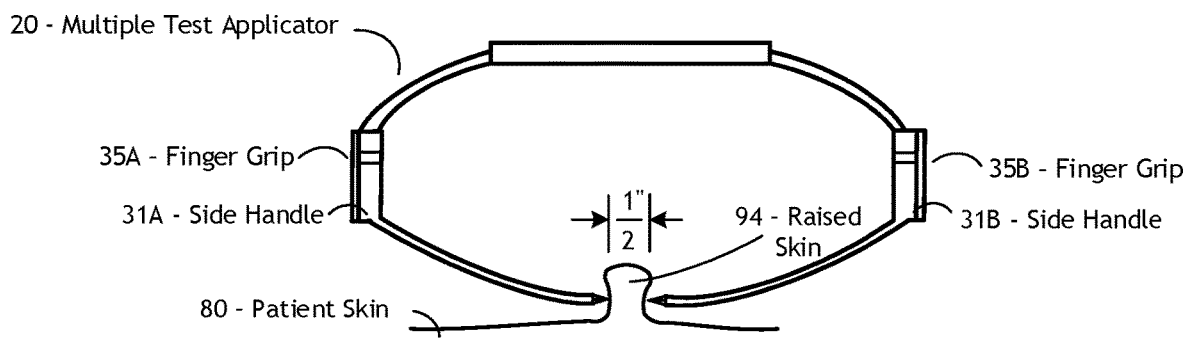
FIG. 6B is a front view of the multiple test applicator of FIG. 6A, the multiple test applicator now being in a compressed position, the pair of opposed scratching barbs resting upon the skin of a patient with each of the scratching barbs disposed at two test sites of the patient, with the skin having been lifted upwards between the pair of opposed scratching barbs.
Figure 6C:
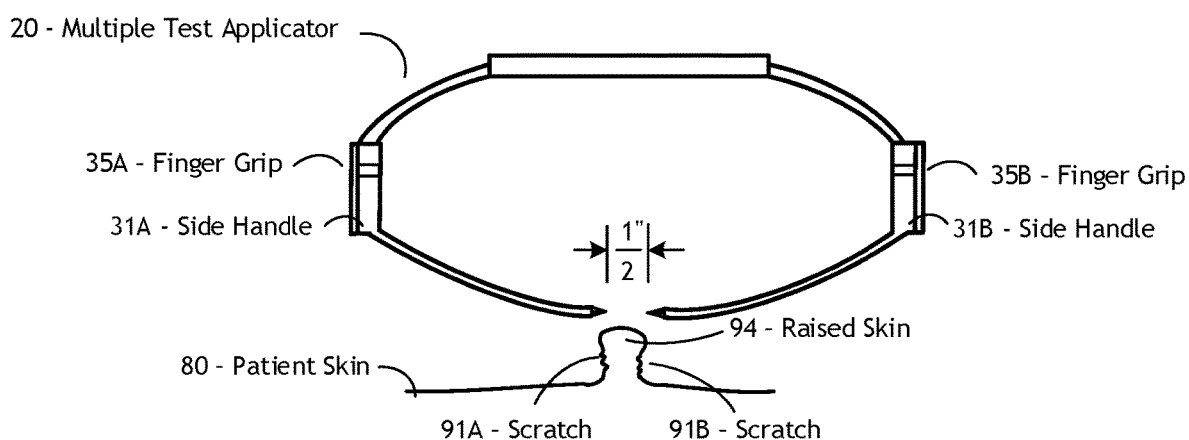
FIG. 6C is a front view of the multiple test applicator of FIG. 6B, the multiple test applicator still being in a compressed position, the pair of opposed scratching barbs now being raised from the skin of the patient with scratches now appearing on each side of the raised skin of the patient.

FIGS. 6A, 6B, and 6C depict the first preferred embodiment of the multiple test applicator [10] of the present invention during allergy barb deposition.

FIG. 6A is a front view of the multiple test applicator [10] in an expanded position, with the scratching barbs [61A and 61B] resting upon the skin of a patient [80]. The scratching barbs [61A and 61B] each include a trace of their respective allergens and are prepared for allergen deposition.

Figure 8A:
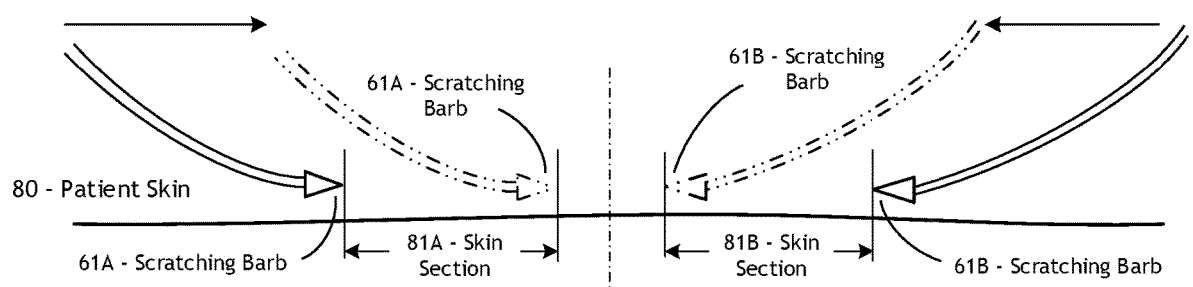
FIG. 8A depicts an exploded view of the first preferred embodiment of the multiple test applicator of the present invention with the scratching barbs pointed upward away from the fluid tray of the multiple test applicator of FIG. 1 as the first and second scratching barbs are positioned upon the skin of the patient in the expanded state, with the compressed state of the first and second scratching barbs shown in phantom.
Figure 8B:
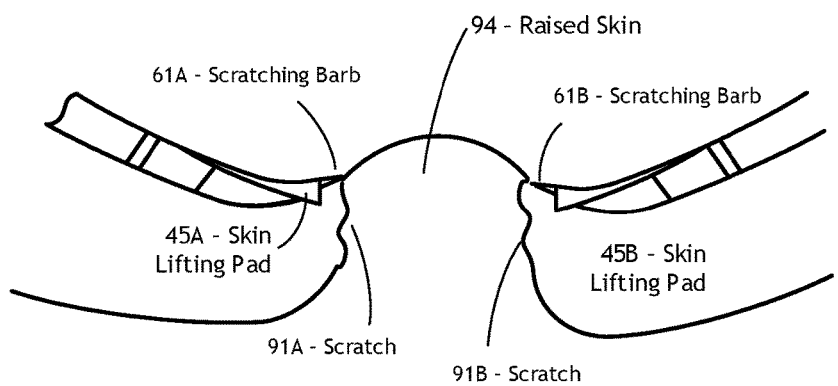
FIG. 8B depicts an exploded side view of a pair of scratching barbs being raised upward on a portion of the skin of a patient that has been pulled together as the scratching barbs generate a pair of scratches, the pair of skin lifting pads being positioned, one on each side of each skin scratching barb, the skin lifting pads lifting the skin and limiting the depth of the penetration of the scratching barb.

FIGS. 6B and 8B depict front views of the multiple test applicator [10]. The multiple test applicator [10] is now being in a compressed position by use of the pair of finger grips [35A and 35B]. The pair of scratching barbs [61A and 61B] are resting upon the skin of the patient [80] and positioned about a portion of the raised skin [94] that has been lifted upwards [94] between the pair of opposed pair of scratching barbs [61A and 61B]. The multiple test applicator [10] is in the allergen deposition position [92].

FIG. 6C is a front view of the multiple test applicator [10]. The multiple test applicator [10] is still being compressed. The pair of scratching barbs [61a and 61B] now have been raised upward from the skin of the patient [80] with a pair of scratches [91A and 91B] now appearing on each side of the portion of the skin of the patient that was lifted upwards [94].

The multiple test applicator [10] comprises a first scratching barb [61A] secured to a first side handle [31A], and a second scratching barb [61B] secured to a second side handle [31B].

The first scratching barb [61A] is cooperatively engaged with a first reservoir [51A] on a fluid tray [50] during allergen loading. A first allergen [71] is retainable in the first reservoir [51A]. The first scratching barb [61A] retains some of the first allergen [71] when removed from the first reservoir [51A] during the allergen loading.

The first and second scratching barbs [61A and 61B] are each projecting in an upward direction away from the fluid tray [50].

The second scratching barb [61B] is cooperatively engaged with a second reservoir [51B] in the fluid tray [50] during the allergen loading. The second scratching barb [61B] opposes the first scratching barb [61A]. The second scratching barb [61B] cooperatively engages with the first scratching barb [61A]. A second allergen is retainable in the second reservoir [51B]. The second scratching barb [61B] retains some of the second allergen [71] when removed from the second reservoir [51B] during the allergen loading.

When subsequently repositioned upon the skin of the patient [80], the scratching barbs [61A and 61B] contact both sides of the raised portion of the skin [94] of the patient. The skin of the patient [80] is raised by the pair of skin lifting pads [45A and 45B], one positioned on each side of each scratching barb [61A and 61B]. Also, the skin lifting pads [45A and 45B] are positioned relative to each scratching barb [61A and 61B] to limit the depth that each scratching barb [61A and 61B] penetrates the skin of the patient [80].

The first side handle [31A] is secured to the first scratching barb [61A] and the second side handle [31B] is secured to the second scratching barb [61B]. The first side handle [31A] opposes the second side handle [31B]. The first side handle [31A] cooperatively engages with the second side handle [31B] such that when inward pressure is applied by an operator holding in one hand the first and second side handles [31A and 31B] during allergen deposition the first scratching barb [61A] is caused to move substantially in a lateral direction across a first section of skin [81A] as the second scratching barb [61B] is caused to move substantially in a lateral direction across a second section of skin [81B] toward the first scratching barb [61A].

The first scratching barb [61A] and the second scratching barb [61B] cooperatively engage to grasp some of the skin of the patient [80]. The first scratching barb [61A] generates a first scratch [91A] and deposits a portion of the first allergen [71] into the first scratch [91A] preferably within the first section of the skin of the patient [81A] as the second scratching barb [61B] generates a second scratch [91B] depositing a portion of the second allergen [71] into the second scratch [91B] preferably within the second section of the skin of the patient [81B].

Then, the multiple test applicator [10] of the present invention is then pulled up and away from the skin of the patient [80]. The operator then waits between 10 to 20 minutes to determine how the patient has reacted to each of these allergens [71]. After the testing has been completed, the physician analyzes the test results to determine the next course of treatment.

With the scratching barbs [61A and 61B] now positioned on the skin of the patient [80], the multiple test applicator [10] is moved from the relaxed state to the compressed state. In so doing, the scratching barbs [61A and 61B] will break the skin of the patient [80] and generate a plurality of small scratches [91A and 91B]. A trace amount of each allergen [71] has been retained on each scratching barb [61A and 61B] and is inserted into each scratch [91A and 91B] on the skin of the patient [80].

The applicator [10] of the present invention for administering the plurality of allergens uses the multiple test system [20] requires allergen loading (the position [25] is depicted in DETAIL "A" of FIG. 1) and allergen deposition (the position [92] is depicted in FIG. 5).

Figure 7A:
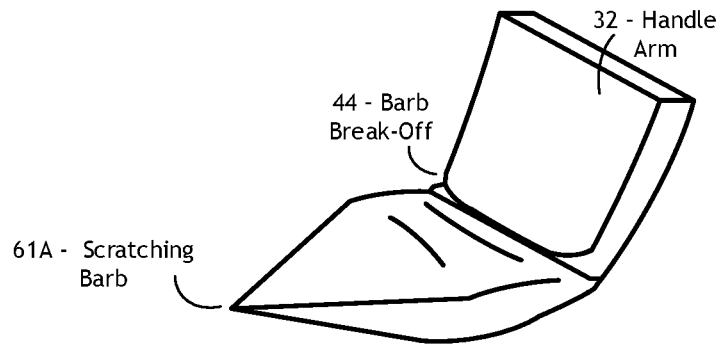
FIG. 7A is an exploded assembly view of the first preferred embodiment of the scratching barb pointed upward away from the fluid tray of the multiple test applicator of FIG. 2, a tip break-off section also being depicted.

FIG. 7A is an exploded assembly view of the first preferred embodiment of the scratching barb pointed upward [61A] toward the spine [21] of the multiple test applicator [10]. A barb break-off section [44] is also shown.

Figure 7B:
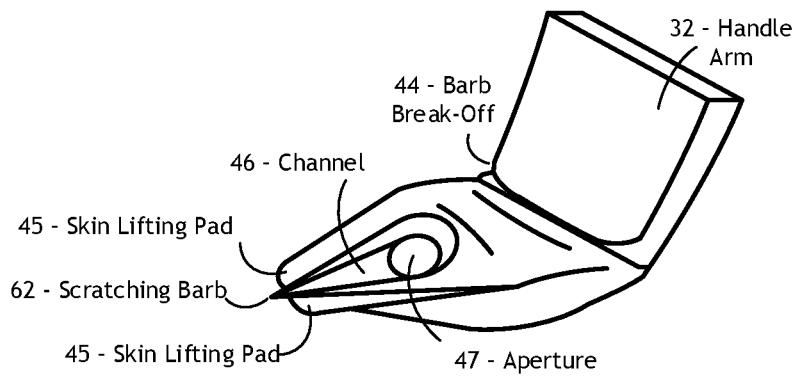
FIG. 7B is an exploded assembly view of a second preferred embodiment of the scratching barb pointed upward away from the fluid tray of the multiple test applicator of FIG. 2, the scratching barb including an aperture and a channel for retaining a trace amount of the allergen, a tip break-off section also being depicted. Skin lifting pads are shown on each side of the barb, the skin lifting pads lifting the skin and limiting the depth of the scratching barb.

FIG. 7B is an exploded assembly view of a second preferred embodiment of the scratching barb pointed upward [62] toward the spine [21] of the multiple test applicator [10]. The scratching barb [62] includes an aperture [47] and a channel [46] for retaining a trace amount of the respective allergen [71]. A barb break-off section [44] is also shown. A pair of skin lifting pads [45A and 45B] are sandwiched about each scratching barb [61A]. The pair of skin lifting pads [45A and 45B] lift the skin and limit the depth of the scratching barb [62]. The pair of skin lifting pads [45A and 45B] controls the depth of the penetration of the scratching barb [62] and ensures repeatability of the testing.

Figure 7C:
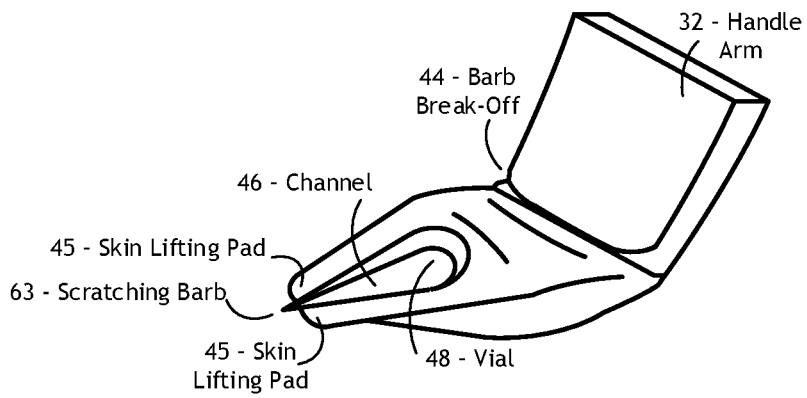
FIG. 7C is an exploded assembly view of a third preferred embodiment of the scratching barb pointed upward away from the fluid tray of the multiple test applicator of FIG. 2, the scratching barb including a vial and a channel for retaining a trace amount of the allergen, a tip break-off section also being depicted. Skin lifting pads are shown on each side of the barb, the skin lifting pads lifting the skin and limiting the depth of the scratching barb.

FIG. 7C is an exploded assembly view of a third preferred embodiment of the scratching barb [63] pointed upward toward the spine [21] of the multiple test applicator [10]. The scratching barb [63] includes a vial [48] and a channel [46] for retaining a trace amount of the respective allergen [71]. A barb break-off section [44] is also shown. A pair of skin lifting pads [45A and 45B] are sandwiched about each scratching barb [63]. The pair of skin lifting pads [45A and 45B] lift the skin and limit the depth of the scratching barb [63]. The pair of skin lifting pads [45A and 45B] control the depth of the penetration of the scratching barbs [63] and ensure repeatability of the testing.

FIG. 8A depicts an exploded view of the first preferred embodiment of the multiple test applicator [10] of the present invention with the scratching barbs pointed upward away from the fluid tray of the multiple test applicator [10]. The first scratching barb [61A] and the second scratching barb [61B] are positioned upon the skin of the patient [80] in the expanded state, with the compressed state of the first scratching barb [61A] and the second scratching barb [61B]

shown in phantom. As the first scratching barb [61A] moves substantially in a lateral direction across a first section of the skin [81A] the second scratching barb [61B] moves substantially in a lateral direction across a second section of the skin [81B] toward the first scratching barb [61A]. As shown in FIG. 8B, the first scratch [91A] is preferably generated in the first section of the skin [81A] as the second scratch [91B] is preferably generated in the second section of the skin [81B].

FIG. 8B depicts an exploded side view of a pair of scratching barbs [61A] being raised upward on a portion of the skin of a patient [80] that has been pulled together and raised [94] as a pair of scratches [91A and 91B] from the pair of scratching barbs [61A and 61B] have been generated. Skin lifting pads [45A and 45B] are shown on both sides of the scratching barb [61A 61B], that lift the skin and limit the depth of penetration of the scratching barb [61A and 61B].

The multiple test applicator [10] including the scratching barbs [61A and 61B] is subsequently transferred to the skin of the patient [80]. Once the multiple test applicator [10] is on the skin of the patient [80], the applicator [10] is moved in such a way, as to lift the skin in front of the scratching barbs [61A and 61B]. The next action is to lift the multiple test applicator [10] perpendicular to the skin of the patient [80], causing the scratching barbs [61A and 61B] containing a trace amount of allergen [71], to scratch the skin through the epidermis in a way so not to penetrate the dermis.

Figure 9:
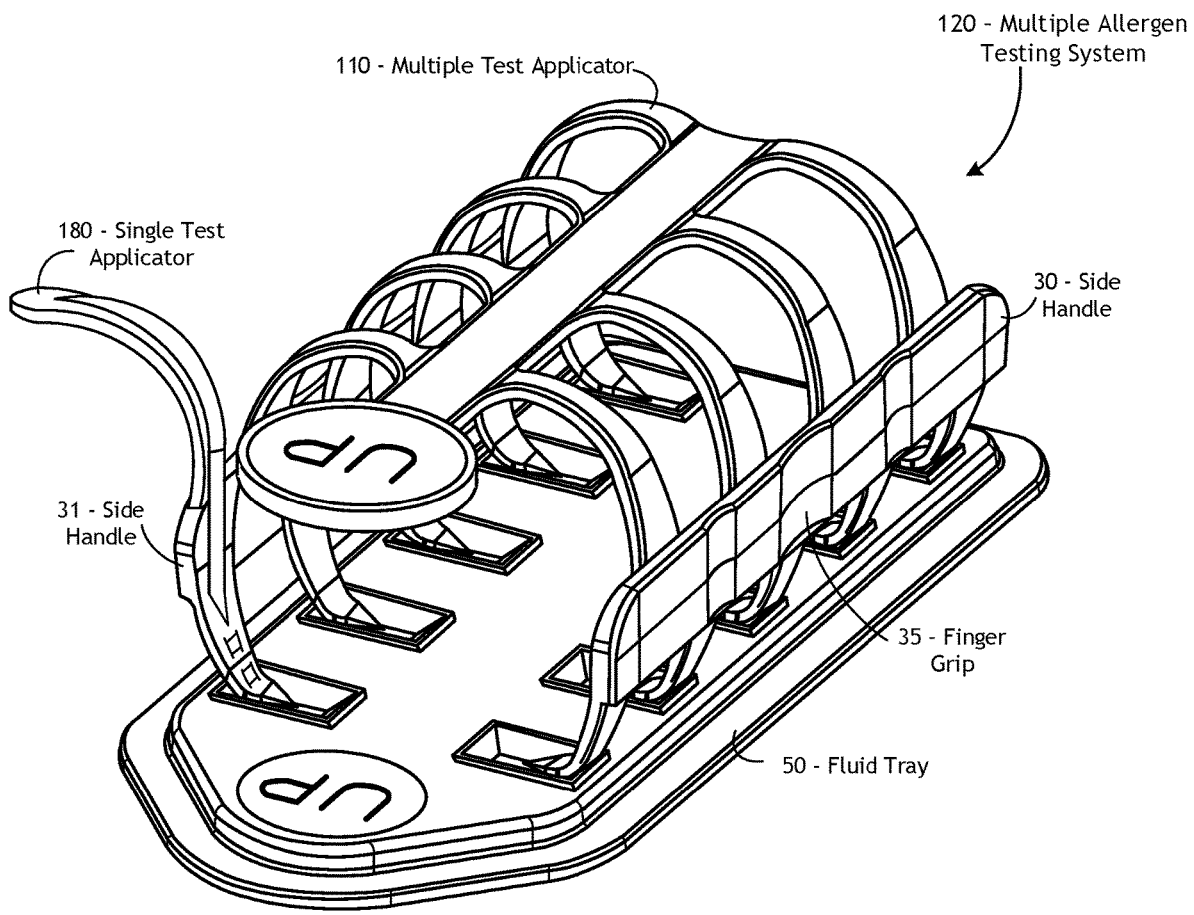
FIG. 9 depicts an assembly view of a second preferred embodiment of the multiple allergen testing system of the present invention comprising a second preferred embodiment of the multiple test applicator of the present invention having nine scratching barbs, and a single test applicator with a one scratching barb, all being cooperatively engaged with ten fluid reservoirs disposed in the fluid tray depicted in FIG. 3.

FIG. 9 depicts an assembly view of a second preferred embodiment of an allergy testing system [120] comprising a second preferred embodiment of the multiple test applicator [110] having nine scratching barbs, and a single test applicator [180] with a single scratching barb, all being in cooperative engagement with ten fluid reservoirs [51A and 51B] in the fluid tray [50]. The multiple test applicator is also compatible with multiple single test applicator units [180] when aligned with a fluid tray [50] that is properly sized with the number and alignment of fluid reservoirs (not shown).

Figures 10A, 10B:
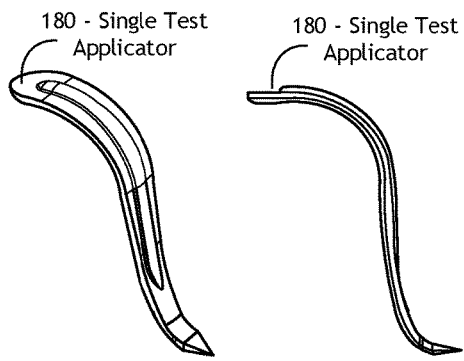
FIG. 10A depicts an assembly view of the single test applicator of FIG. 9.

FIG. 10A depicts an assembly view of the single test applicator [180], and FIG. 1013 depicts an end view of the single test applicator [180].

FIG. 11 thru 15 disclose a second preferred embodiment for using the multiple test applicator [210] of the present invention for allergy skin testing.

The multiple test applicator [210] comprises a first scratching barb [261A] secured to a first side handle [31A], and a second scratching barb [261B] secured to a second side handle [31B].

The first scratching barb [261A] is cooperatively engageable with a first reservoir [51A] on a fluid tray [50] during allergen loading. A first allergen [71] is retainable in the first reservoir [51A]. The first scratching barb [261A] retains some of the first allergen [71] when removed from the first reservoir [51A] during the allergen loading.

The second scratching barb [261B] is cooperatively engageable with a second reservoir [51B] in the fluid tray [50] during the allergen loading. The second scratching barb [261B] opposes the first scratching barb [261A]. The second scratching barb [261B] cooperatively engages with the first scratching barb [261A]. A second allergen [71] is retainable in the second reservoir [51B]. The second scratching barb [261B] retains some of the second allergen [71] when removed from the second reservoir [51B] during the allergen loading.

The first side handle [31A] secured to the first scratching barb [261A] and a second side handle [31B] secured to the second scratching barb [261B]. The first side handle [31A] opposes the second side handle [31B]. The first side handle [31A] cooperatively engages with the second side handle [31B] as inward pressure is applied by an operator holding in one hand the first side handle [31A] and the second side handle [31B] after the allergen loading is completed and prior to the allergen deposition. The first scratching barb [261A] and the second scratching barb [261B] are placed on skin of the patient [80]. The inward pressure is then released during the allergen deposition such that the first scratching barb [261A] moves substantially in a lateral direction across a first section of the skin of the patient [281A] as the second scratching barb [261B] moves substantially in a lateral direction across a second section of the skin of the patient [281B] away from the first scratching barb [261A]. The first scratching barb [261A] generates a first scratch [291A] depositing a portion of the first allergen [71] into preferably a first section of skin [281A] the first scratch [291A] as the second scratching barb [261B] generates a second scratch [291B] depositing a portion of the second allergen [71] preferably into preferably a second section of skin [281B] of the second scratch [291B].

Figure 11:
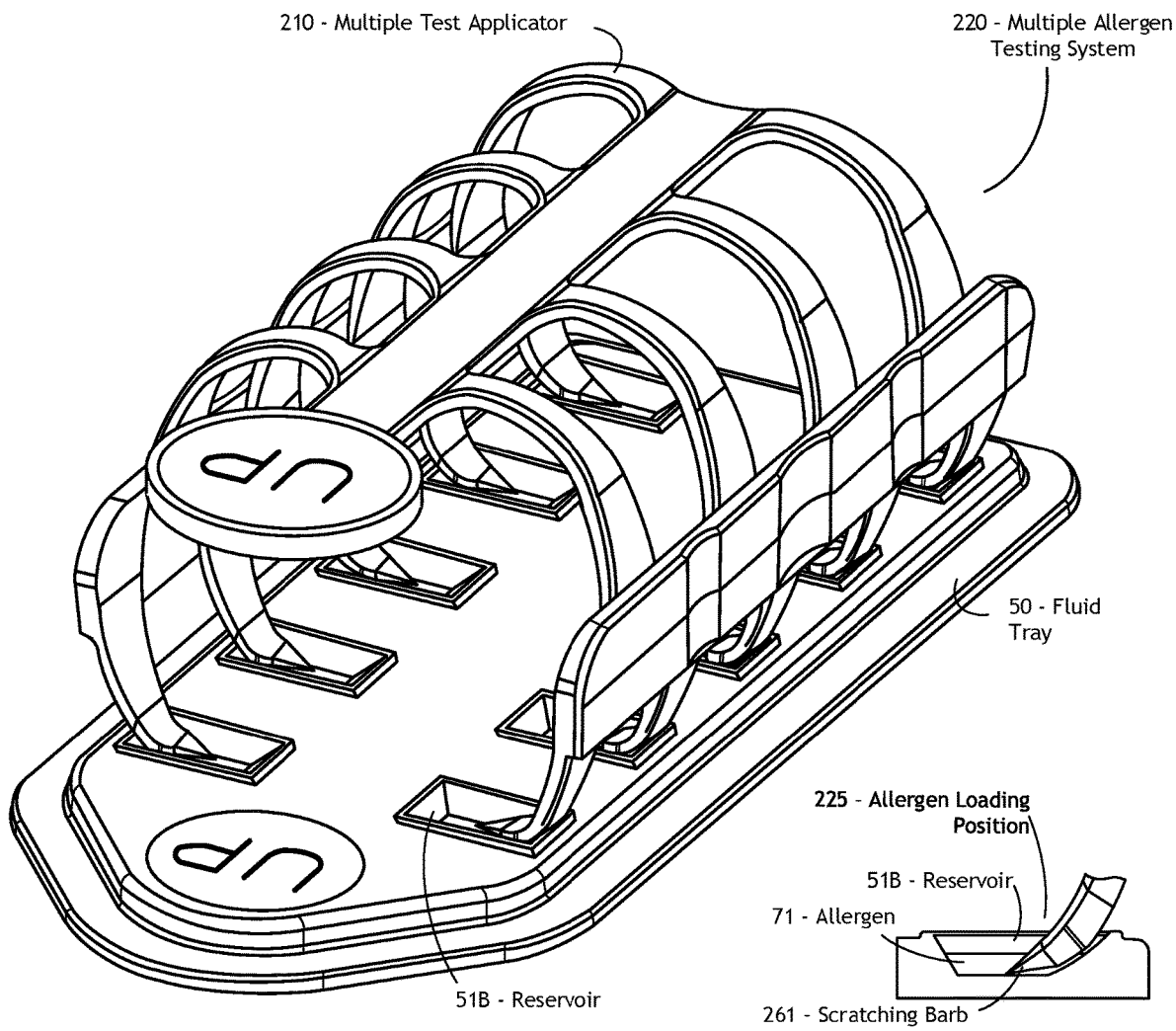
FIG. 11 depicts an assembly view of a third preferred embodiment of the multiple allergen testing system of the present invention comprising a third preferred embodiment of the multiple test applicator having ten scratching barbs cooperatively engaged with ten reservoirs of a fluid tray of FIG. 3, the multiple test applicator being disposed on the fluid tray; and DETAIL "B" depicts an exploded side view of the scratching barb positioned in the reservoir of the fluid tray pointing downward relative to the fluid tray, the reservoir being partially filled with allergen.

FIG. 11 depicts an assembly view of a third preferred embodiment of multiple allergen testing system [220] comprising of a third preferred embodiment of the multiple test applicator [210] including a first scratching barb [261A] in cooperative engagement a first fluid reservoirs [51A] and a second scratching barb [261B] in cooperative engagement with a second fluid reservoir [51B] both fluid reservoirs [51A and 51B] positioned in a fluid tray [50].

DETAIL "B" depicts an exploded side view of the scratching barb [261B] positioned in a reservoir [51B] of the fluid tray [50] while in the allergen loading position. The reservoir [51B] is partially filled with allergen [71]. Here, the scratching barbs [261A and 261B] project in a downward direction pointing to the bottom of the fluid tray [50]. The multiple test applicator [210] is enabled to reposition from the compressed state to the relaxed state when placed on the skin of the patient [80] during allergen deposition [92].

Figure 12:
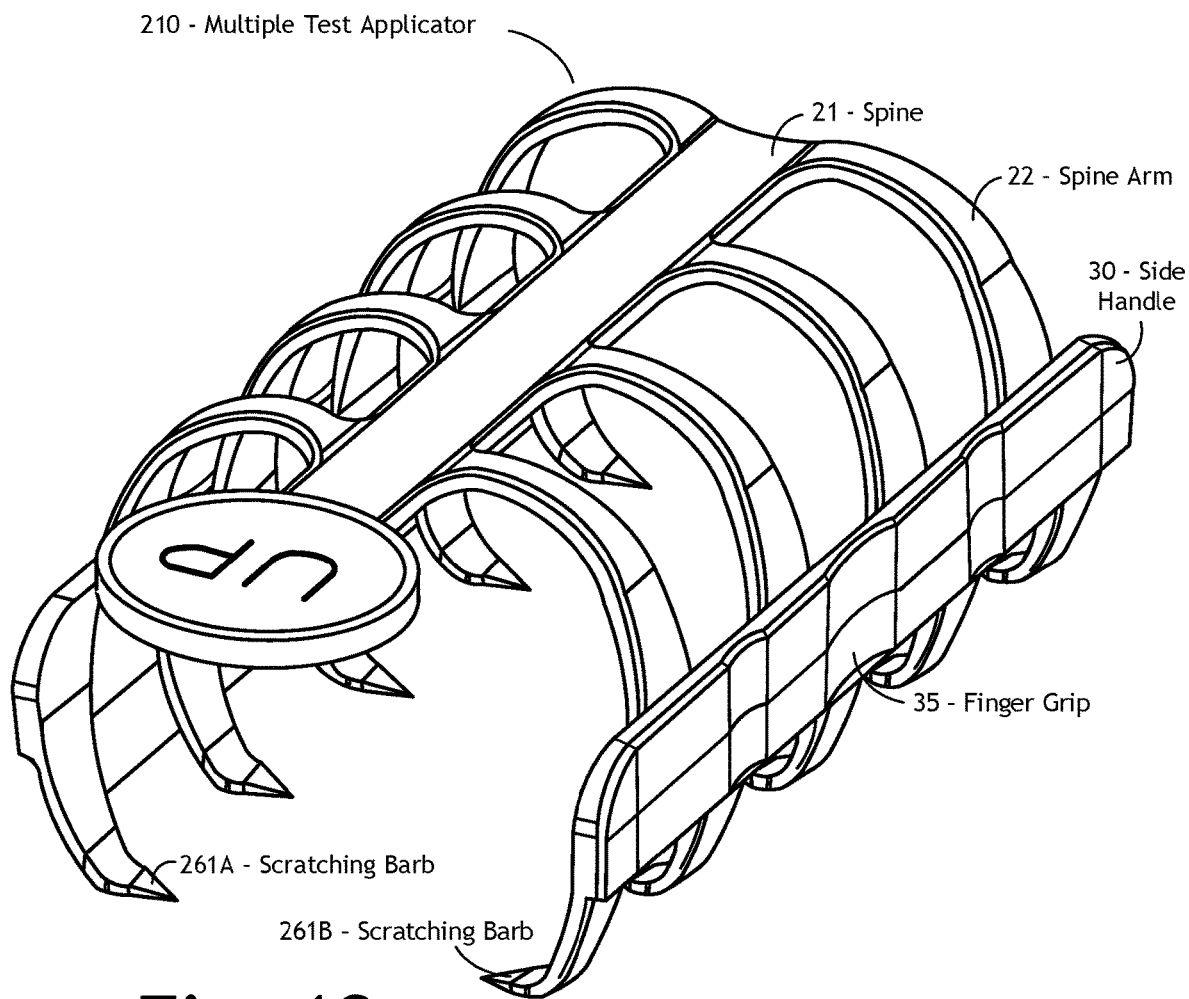
FIG. 12 depicts the third preferred embodiment of the multiple test applicator of FIG. 11.

FIG. 12 depicts the third preferred embodiment of the multiple test applicator [220] of the present invention.

Figure 13A:
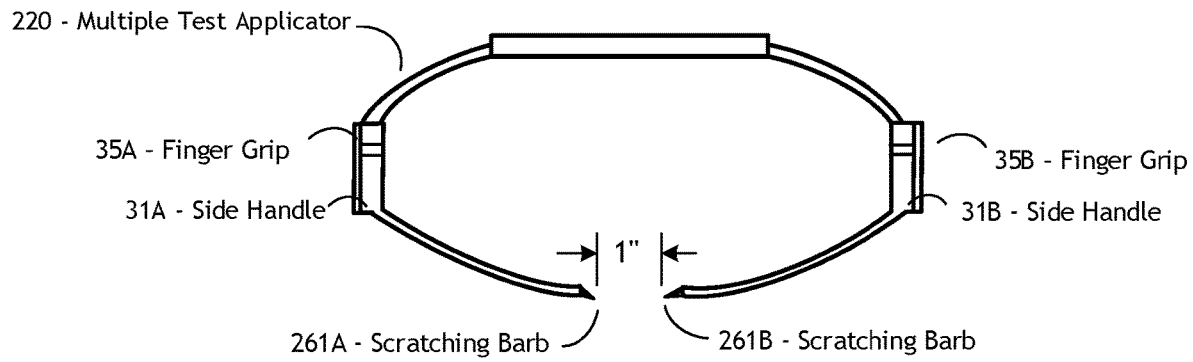
FIG. 13A is a front view of the multiple test applicator in a relaxed state, the scratching barbs now being loaded, and each scratching barb including a trace of their respective fluids and are now prepared for allergen deposition.
Figure 13B:
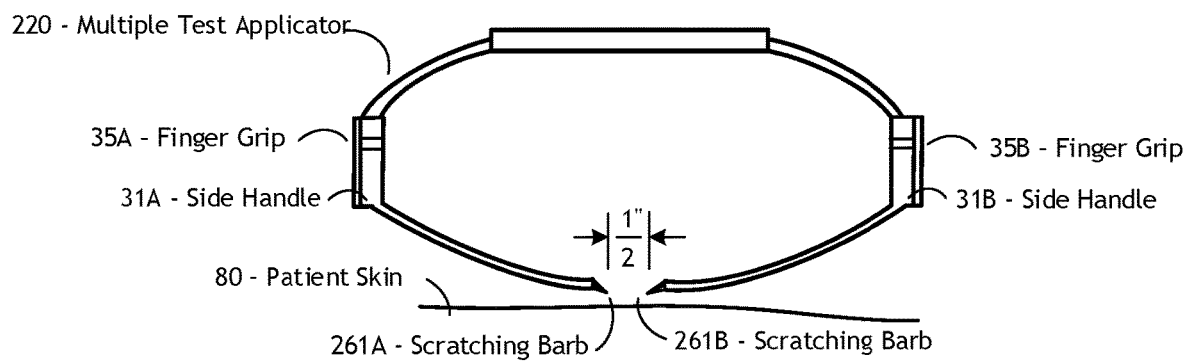
FIG. 13B is a front view of the multiple test applicator of FIG. 13A, the multiple test applicator now being in a compressed state. The scratching barbs are resting upon the skin of a patient with the each of two scratching barbs pointed downward.
Figure 13C:
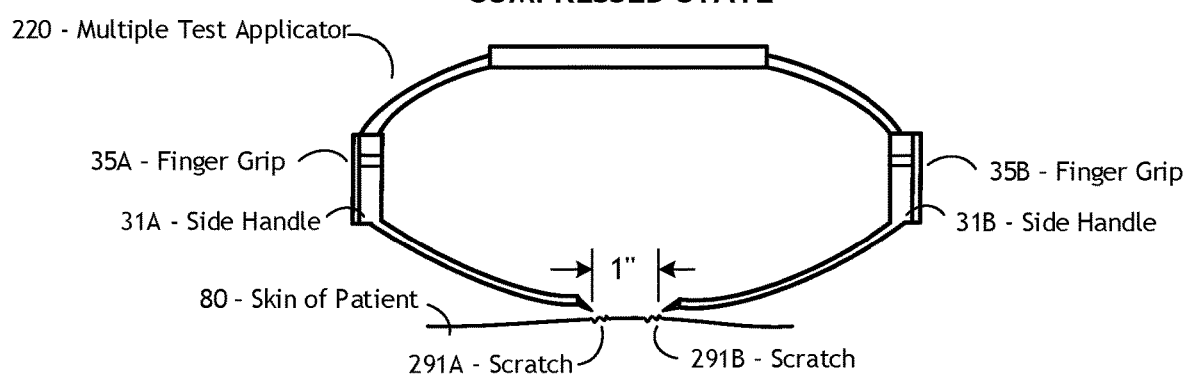
FIG. 13C is a front view of the multiple test applicator of FIG. 13B, the multiple test applicator now being in an expanded state, the scratching barbs now have generated a pair of scratches at a pair of test sites as the scratching barbs move away from each other.

FIGS. 13A, 13B, and 13C depict the first preferred embodiment of the multiple test applicator [210] of the present invention during allergy barb deposition [92]. Each of the scratching barbs [261A or 261B] of the multiple test applicator [220] are pointing downward toward the bottom of the fluid tray [50] when disposed in the fluid tray [50]. Again, the fluid tray [50] contains multiple allergens, generally test fluid in each reservoir [51A and 51B]. Allergens [71] are initially selected and placed into containment reservoirs [51A and 51B] in the fluid tray [50], and care is taken not to use an excess amount of the allergens. After allergen loading is completed, the operator lifts the multiple test applicator [220] out of the fluid tray [50], the multiple test applicator [210] being in the relaxed state. Using the pair of opposing finger grips [35A and 35B], the operator applies pressure moving the multiple test applicator [220] to a compressed state before placing the applicator [220] upon the skin of the patient [80] in the allergen deposition position, the operator pushes lightly upon the applicator [220] and slowly releases the finger grips [35A and 35B]. This generates a pair of scratches [291A and 291B] at each test site essentially simultaneously on the skin of the patient [80]. Trace amounts of each respective allergen [71] then seep into each respective scratch [291A or 291B]. The use of the finger grips [35A and 35B] to move the multiple test applicator [220] from the relaxed state to the compressed state and then back again to the relaxed state enables one-handed operation by the operator. Then, the multiple test applicator [220] is pulled up and away from the skin of the patient [80].

FIG. 13A is a front view of the multiple test applicator [210] in an expanded position, with the scratching barbs [261A and 261B] resting upon the skin of a patient [80]. The scratching barbs [261A and 261B] each include a trace of their respective allergens and are prepared for allergen deposition.

After allergen loading is completed, the operator lifts the multiple test applicator [220] out of the fluid tray [50], the multiple test applicator [210] being in the relaxed state. Using the pair of opposing finger grips [35A and 35B], the operator applies pressure moving the multiple test applicator [220] to a compressed state before placing the applicator [220] upon the skin of the patient [80] in the allergen deposition position, the operator pushes lightly upon the applicator [220] and slowly releases the finger grips [35A and 35B].

Figure 15:
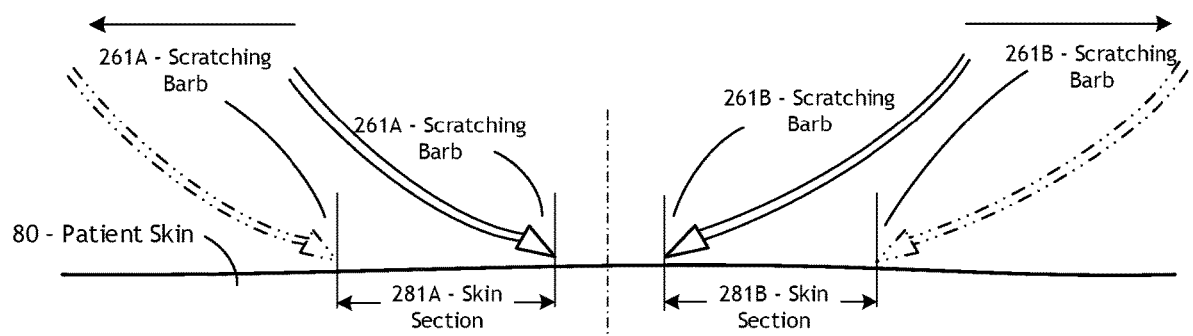
FIG. 15 depicts an exploded view of the third preferred embodiment of the multiple test applicator of the present invention with the scratching barbs pointed downward toward bottom of the fluid tray as the first and second scratching barbs are positioned upon the skin of the patient in the compressed state (with the expanded state of the first and second scratching barbs shown in phantom) as the first scratching barb moves laterally across a first section of the skin as the second scratching barb moves laterally across a second section of the skin away from the first scratching barb, the first scratch being preferably generated in the first section of the skin as the second scratch is preferably generated in the second section of the skin.

FIGS. 13B and 15 depict front views of the multiple test applicator [210]. The multiple test applicator [10] is now being in a compressed position by use of the pair of finger grips [35A and 35B]. The pair of scratching barbs [261A and 261B] are resting upon the skin of the patient [80] and positioned upon the skin of the patient [80] and released.

FIG. 13C is a front view of the multiple test applicator [210]. As the pair of scratching barbs [261A and 261B] are released to a relaxed state, the first scratching barbs [261A] has generated a first scratch [291A] as the second scratching barb [2261B] has generated a second scratch [291B]. A first scratch [291A] is preferably generated in a first section of the skin [281A] as the second scratch [291B] is generated in the second section of the skin [281B].

Then, the operator waits between 10 to 20 minutes to determine how the patient has reacted to these allergens. After the testing has been completed, the physician analyzes the test results to determine the next course of treatment.

Figure 14A:
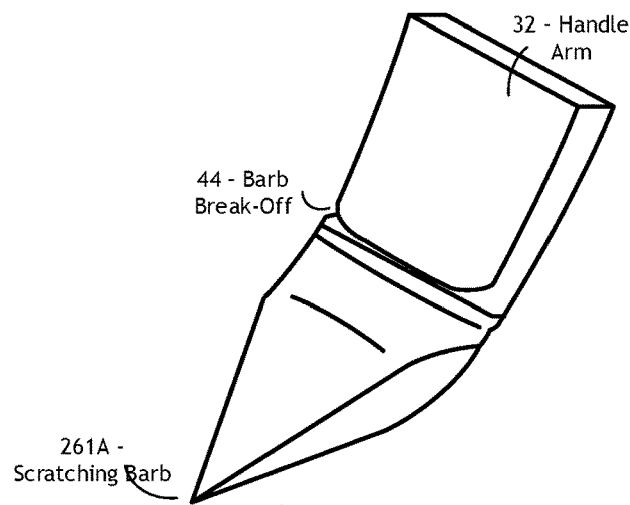
FIG. 14A is an exploded assembly view of the first preferred embodiment of the scratching barb pointed downward toward the fluid tray of FIG. 3, a tip break-off section also being depicted.

FIG. 14A is an exploded assembly view of the first preferred embodiment of the scratching barbs [261A and 261B] pointed downward toward from the fluid tray [50] of the multiple test applicator [220]. A barb break-off section [44] also being shown.

Figure 14B:
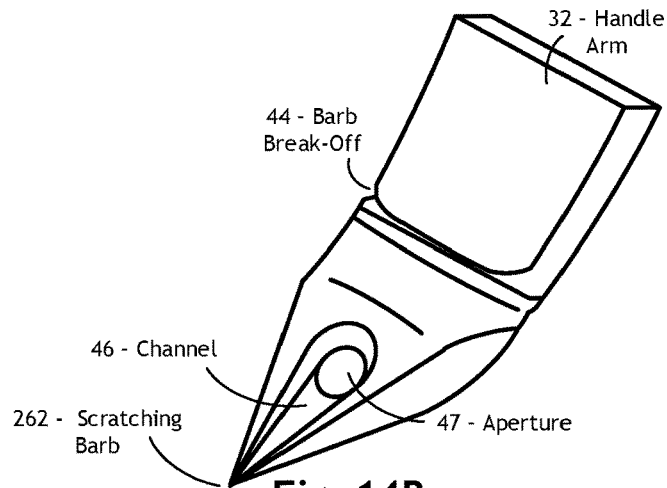
FIG. 14B is an exploded assembly view of a second preferred embodiment of the scratching barb pointed downward toward from the fluid tray of FIG. 3, the scratching barb including an aperture and a channel for retaining a trace amount of the allergen, a tip break-off section also being depicted.

FIG. 14B is an exploded assembly view of a second preferred embodiment of the scratching barb [262] pointed downward away from the spine [21] of the multiple test applicator [210], the scratching barb [262] including an aperture [47] and a channel [46] for retaining a trace amount of the allergen [71]. A barb break-off section [44] also being shown.

Figure 14C:
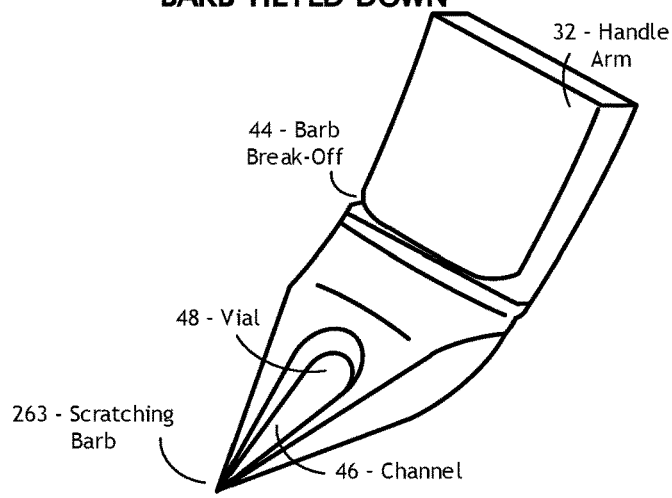
FIG. 14C is an exploded assembly view of a third preferred embodiment of the scratching barb pointed downward toward from the fluid tray of FIG. 3, the scratching barb including a vial and a channel for retaining a trace amount of the allergen, a tip break-off section also being depicted.

FIG. 14C is an exploded assembly view of a third preferred embodiment of the scratching barb [263] pointed downward away from the spine [21] of the multiple test applicator [220], the scratching barb [263] including a vial [48] and a channel [46] for retaining a trace amount of the allergen [71], a break-off section also being shown. A barb break-off section [44] also being shown.

FIG. 15 depicts an exploded view of the third preferred embodiment of the multiple test applicator [210] of the present invention with the scratching barbs [261A and 281B] pointed downward toward bottom of the fluid tray [50] as the first and second scratching barbs are positioned upon the skin of the patient in the compressed state, with the expanded state of the first and second scratching barbs shown in phantom. As the first scratching barb [261A] moves substantially in a lateral direction across a first section of the skin [281A] as the second scratching barb [261B] moves substantially in a lateral direction across a second section of the skin [281B] away from the first scratching barb [261A]. As shown in FIG. 13C, the first scratch [291A] is preferably generated in the first section of the skin [281A] as the second scratch [291B] is preferably generated in the second section of the skin [281B].

Application barb loading is similar to the procedure already discussed in detail. Once allergen loading is completed, the multiple test applicator [210] is removed from the fluid tray [50] and repositioned onto the skin (i.e.—arm, back, or leg) of the patient [80].

In the allergen deposition position, the multiple test applicator [210] is compressed, and each allergen [71] is deposited into each respective scratch [91A and 91B] generated by each respective scratching barb [61A and 61B] on the skin of the patient [80] for further analysis as needed by the treating physician.

After the prescribed time between 10 to 20 minutes the test operator records the skin condition with a photo of each scratch site. The applicator includes break-off features for the arms, legs, and tips enabling more efficient disposal of the device after use with a patient. The break-off features for the tips enable this part of the applicator to be disposed of in a biohazard sharps container. The leg break-off points enable the legs to be broken off from the spine and the legs and spine to be disposed of in a separate container from the tips. The fluid tray can also be disposed of in the same container. This increases the packing density of the discarded material and a much lower disposal cost.

Also, the multiple test applicator [10] has the advantage of breaking the skin of the patient without downward pressure. This diminishes chances of the mast cells (histamine containing cells) releasing the histamine secondary to pressure causing a false positive. This may be a critical factor with percutaneous allergy testing.

The single and multiple allergen testing system [120] enables testing for a single allergy or multiple allergies in the same device. The allergen testing applicator [110] simulates the best practice in a controlled procedure. The multiple-allergen testing system is designed around a multiple allergen testing system [120] that enables the accurate and repeatable placement of allergy testing fluid, either in a tray or on the skin of a patient. The testing procedure also controls the scratching or pricking of the skin, to introduce the allergen in a more controlled manner.

The multiple test applicator [10, 110, and 210] and the fluid tray [50] are preferably made of engineering grade polymers that are sterilized prior to use in an autoclave, or other standard sterilization procedures. Hence, the materials preferably are made of plastics that are stable at higher temperatures. The multiple test applicator is depicted having ten scratching barbs. The multiple applicator unit may also have two, four, six, eight, twelve, and any of a wide variety of configurations, as needed.

It is critical during use that the allergens [71] for the various reservoirs [51A and 51B] do not become intermixed as this contamination will affect the test results. The suggested minimum distance between two neighboring scratching barbs extending from the same side frame is preferably at least three-quarters of an inch.

It is critical that the multiple test applicator be held in one hand of the operator who is administering the test. This will enable the other hand to be free to take notes, to assist the patient, or do whatever becomes necessary during the administration of the procedure.

Accordingly, the multiple test applicator [10] preferably has ten scratching barbs as depicted and is preferably about 2" (height)×2" (width)×5" (length). If the multiple test applicator has eight scratching barbs (2×4), the length is preferably 3.75" to 4.50" in length, if the multiple test applicator has twelve scratching barbs (2×6), the length is about 5.00 to 5.50", etc. It is to be understood that while the multiple allergen testing device as depicted in the accompanying drawings depicts a unit with ten testing devices, one skilled in the art can readily modify this geometry to include 4, 6, 8, 12, 16, 20, 24, 30, 36, or any other combination of multiple testing devices, this disclosure is being limited to 10 for purposes of illustration only.

The multiple test applicator [10] enables testing for multiple allergies in one device and one test procedure or one test with the single tester and one allergy testing fluid. The most consistent results have been achieved by inserting a drop of allergy testing fluid on the skin and then scratching the skin with a simple needle (best practice). The multiple test applicator [10] of the present invention duplicates the best practice but in a controlled, repeatable, and reproducible way. The system built around the devices enables the accurate and repeatable placement of the allergy testing fluid, in a tray and transfers this fluid to the multiple test applicator [10] or the single test applicator [180], by placing the testing end of the device, into the fluid tray [50]-After the prescribed time between 10 to 20 minutes the medical technician records the skin condition. The applicator includes break-off features for the arms, legs, and tips enabling more efficient disposal of the device after use with a patient. The break-off features for the tips enable this part of the applicator to be disposed of in a biohazard sharps container. The leg break-off points enable the legs to be broken off from the spine and the legs and spine to be disposed of in a separate container from the tips. The fluid tray [50] can also be disposed of in the same container. This increases the packing density of the discarded material and a much lower disposal cost.

Also, the multiple test applicator [10] has the advantage of breaking the skin of the patient [80] without downward pressure. This diminishes chances of the mast cells (histamine containing cells) releasing the histamine secondary to pressure causing a false positive. This may be a critical factor with percutaneous allergy testing.

Throughout this application, various Patents and Applications are referenced by number and inventor. The disclosures of these documents in their entireties are hereby incorporated by reference into this specification in order to more fully describe the state of the art to which this invention pertains.

It is evident that many alternatives, modifications, and variations of the multiple test applicator of the present invention will be apparent to those skilled in the art in lieu of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

PARTS LIST

10. Multiple Test Applicator—1$^{st}$ Embodiment
20. Multiple Allergen Testing System—1$^{st}$ Embodiment
21. Spine
22. Spine Arm
25. Allergen loading Position
31A and 31B. Side Handles
33A and 33B. Handle Arms
35A and 35B. Finger Grips
44. Barb Break-Off
45A and 45B. Skin Lifting Pads
46. Channel
47. Aperture
48. Vial
50. Fluid Tray
51A and 51B. Reservoirs
61A and 61B. Scratching Barbs
64. Alternate Scratching
64. Alternate Scratching
71. Allergen
80. Patient Skin
81A and 81B. Skin Sections
91A and 91B. Scratches
93. Allergen Deposition Position
94. Raised Skin
96. Hand of Medical Technician
110. Multiple Test Applicator—2$^{nd}$ Embodiment
120. Multiple Allergen Testing System—2$^{nd}$ Embodiment
180. Single Unit Applicator
210. Multiple Test Applicator—3$^{rd}$ Embodiment
220. Multiple Allergen Testing System—3$^{rd}$ Embodiment
225. Allergen loading Position
261A and 261B. Scratching Barb
262. Scratching Barb
263. Scratching Barb
281A and 281B. Skin Sections
291A and 291B. Scratches

The invention claimed is:

1. A multiple test applicator comprising:
a first scratching barb being cooperatively engageable with a first reservoir on a fluid tray during allergen loading, a first allergen being retainable in said first reservoir, said first scratching barb retaining some of a first allergen when removed from said first reservoir during said allergen loading; and
a second scratching barb being cooperatively engageable with a second reservoir on said fluid tray during said allergen loading, said second scratching barb opposing said first scratching barb, said second scratching barb cooperatively engaging with said first scratching barb, a second allergen being retainable in said second reservoir, said second scratching barb retaining some of said second allergen when removed from said second reservoir during said allergen loading; and
a first side handle secured to said first scratching barb, a second side handle secured to said second scratching barb, said first side handle opposing said second side handle, said first side handle and said second side handle configured to fit into one hand of an operator, said first side handle cooperatively engaging with said second side handle such that application of inward pressure on said first side handle and said second side handle during allergen deposition causes said first scratching barb to move in a lateral direction across a first section of skin as said second scratching barb moves in a lateral direction across a second section of skin toward said first scratching barb, said first scratching barb and said second scratching barb grasping some of said skin, said first scratching barb generating a first scratch and depositing a portion of said first allergen into said first scratch as said second scratching barb generates a second scratch depositing a portion of said second allergen into said second scratch.

2. The multiple test applicator of claim 1, wherein said first scratching barb is sandwiched between a first pair of skin lifting pads.

3. The multiple test applicator of claim 1, wherein said first scratching barb is sandwiched between a first pair of skin lifting pads and said second scratching barb is sandwiched between a second pair of skin lifting pads, said first pair of skin lifting pads grasping and lifting said first section as said second pair of skin lifting pads grasp and lift said second section.

4. The multiple test applicator of claim 1, wherein said first scratch is generated in said first section of said skin as said second scratch is generated in said second section of said skin.

5. The multiple test applicator of claim 1, wherein said first scratch is generated in said first section of said skin.

6. The multiple test applicator of claim 1, wherein releasing of said inward pressure applied to said first side handle and said second side handle facilitates movement of said first scratching barb away from said second scratching barb.

7. The multiple test applicator of claim 1, wherein as said inward pressure is applied to said first scratching barb and said second scratching barb grasping a portion of said skin of said patient, said first scratch and said second scratch appear on each side of said portion of said skin of said patient.

8. A multiple test applicator comprising:
a first scratching barb being cooperatively engageable with a first reservoir on a fluid tray during allergen loading, a first allergen being retainable in said first reservoir, said first scratching barb retaining some of a first allergen when removed from said first reservoir during said allergen loading;
a second scratching barb being cooperatively engageable with a second reservoir on said fluid tray during said allergen loading, said second scratching barb opposing said first scratching barb, said second scratching barb cooperatively engaging with said first scratching barb, a second allergen being retainable in said second reservoir, said second scratching barb retaining some of said second allergen when removed from said second reservoir during said allergen loading; and
a first side handle secured to said first scratching barb, a second side handle secured to said second scratching barb, said first side handle opposing said second side handle, said first side handle and said second side handle configured to fit into one hand of an operator, said first side handle cooperatively engaged with said second side handle as inward pressure is applied on said first side handle and said second side handle after said allergen loading is completed and prior to said allergen deposition, where said first scratching barb and said second scratching barb are placed on skin as said inward pressure is released during said allergen deposition such that said first scratching barb moves in a lateral direction across a first section of said skin as said second scratching barb moves in a lateral direction across a second section of said skin away from said first scratching barb, said first scratching barb generating a first scratch depositing a portion of said first allergen into said first scratch as said second scratching barb generates a second scratch depositing a portion of said second allergen into said second scratch.

9. The multiple test applicator of claim 8, wherein said first scratch is generated in said first section of said skin as said second scratch is generated in said second section of said skin.

10. The multiple test applicator of claim 8, wherein said first scratch is generated in said first section of said skin.

11. The multiple test applicator of claim 8, wherein application of said pressure in an inward direction of said first side handle toward said second side handle facilitates movement of said first scratching barb toward said second scratching barb.

12. The multiple test applicator of claim 8, wherein release of said pressure applied in an inward direction of said first side handle toward said second side handle facilitates movement of said first scratching barb away from said second scratching barb.

13. A multiple test applicator comprising:
a first scratching barb being cooperatively engageable with a first reservoir on a fluid tray during allergen loading, a first allergen being retainable in said first reservoir, said first scratching barb retaining some of a first allergen when removed from said first reservoir during said allergen loading;
a second scratching barb being cooperatively engageable with a second reservoir on said fluid tray during said allergen loading, said second scratching barb opposing said first scratching barb, said second scratching barb cooperatively engaging with said first scratching barb, a second allergen being retainable in said second reservoir, said second scratching barb retaining some of said second allergen when removed from said second reservoir during said allergen loading; and
a first side handle secured to said first scratching barb, a second side handle secured to said second scratching barb, said first side handle opposing said second side handle, said first side handle and said second side handle configured to fit into one hand of an operator, said first side handle cooperatively engaged with said second side handle such that application of pressure on said first side handle and said second side handle during allergen deposition causes said first scratching barb to move in a lateral direction across a first section of said skin as said second scratching barb moves in a lateral direction across a second section of said skin, said first scratching barb generating a first scratch in said first section of said skin depositing a portion of said first allergen into said first scratch as said second scratching barb generates a second scratch depositing a portion of said second allergen into said second scratch.

14. The multiple test applicator of claim 13, wherein said first scratching barb is sandwiched between a first pair of skin lifting pads.

15. The multiple test applicator of claim 13, wherein said first scratching barb is sandwiched between a first pair of skin lifting pads and said second scratching barb is sandwiched between a second pair of skin lifting pads, said first pair of skin lifting pads grasping and lifting said first section as said second pair of skin lifting pads grasp and lift said second section.

16. The multiple test applicator of claim 13, wherein said first scratch is generated in said first section of said skin as said second scratch is generated in said second section of said skin.

17. The multiple test applicator of claim 13, wherein said first scratch is generated in said first section of said skin.

18. The multiple test applicator of claim 13, wherein application of said pressure in an inward direction of said first side handle toward said second side handle facilitates movement of said first scratching barb toward said second scratching barb.

19. The multiple test applicator of claim 13, wherein release of said pressure applied in an inward direction of said first side handle toward said second side handle facilitates movement of said first scratching barb away from said second scratching barb.

20. A multiple test applicator comprising:
- a first scratching barb being cooperatively engageable with a first reservoir on a fluid tray during allergen loading, a first allergen being retainable in said first reservoir, said first scratching barb retaining some of a first allergen when removed from said first reservoir during said allergen loading;
- a second scratching barb being cooperatively engageable with a second reservoir on said fluid tray during said allergen loading, said second scratching barb opposing said first scratching barb, said second scratching barb cooperatively engaging with said first scratching barb, a second allergen being retainable in said second reservoir, said second scratching barb retaining some of said second allergen when removed from said second reservoir during said allergen loading; and
- a first side handle secured to said first scratching barb, a second side handle secured to said second scratching barb, a first finger grip being coupled to said first side handle, a second finger grip coupled to said second side handle, said first side handle and said second side handle configured to fit into one hand of an operator, said first finger grip opposing said second finger grip such that when inward pressure is applied by squeezing together said first finger grip toward said second finger grip during allergen deposition, said first scratching barb cooperatively engages with said second scratching barb, said first scratching barb moves in a lateral direction across a first section of said skin as said second scratching barb moves in a lateral direction across a second section of said skin, said first scratching barb generating a first scratch depositing a portion of said first allergen into said first scratch as said second scratching barb generates a second scratch depositing a portion of said second allergen into said second scratch.

21. The multiple test applicator of claim 20, wherein said first scratching barb is sandwiched between a first pair of skin lifting pads.

22. The multiple test applicator of claim 20, wherein said first scratching barb is sandwiched between a first pair of skin lifting pads and said second scratching barb is sandwiched between a second pair of skin lifting pads, said first pair of skin lifting pads grasping and lifting said first section as said second pair of skin lifting pads grasp and lift said second section.

23. The multiple test applicator of claim 20, wherein said first scratch is generated in said first section of said skin as said second scratch is generated in said second section of said skin.

24. The multiple test applicator of claim 20, wherein said first scratch is generated in said first section of said skin.

25. The multiple test applicator of claim 20, wherein application of said inward pressure of said first finger grip toward said second finger grip facilitates movement of said first scratching barb toward said second scratching barb.

26. The multiple test applicator of claim 20, wherein release of said inward pressure of said first finger grip toward said second finger grip facilitates movement of said first scratching barb away from said second scratching barb.

* * * * *